US006238346B1

(12) United States Patent
Mason

(10) Patent No.: US 6,238,346 B1
(45) Date of Patent: May 29, 2001

(54) SYSTEM AND METHOD EMPLOYING TWO DIMENSIONAL ULTRASOUND ARRAY FOR WIDE FIELD OF VIEW IMAGING

(75) Inventor: Martin K Mason, Andover, MA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/344,100

(22) Filed: Jun. 25, 1999

(51) Int. Cl.[7] ................................................ A61B 8/14
(52) U.S. Cl. ............................................................ 600/459
(58) Field of Search ............................ 600/437, 443, 600/447, 459; 73/625, 626; 367/103, 105, 118, 138

(56) References Cited

U.S. PATENT DOCUMENTS

| 4,112,411 | * | 9/1978 | Alais et al. ....................... 340/1 R |
| 5,427,106 | | 6/1995 | Breimesser et al. . |
| 5,460,180 | | 10/1995 | Klepper et al. . |
| 5,490,512 | * | 2/1996 | Kwon et al. ...................... 600/447 |
| 5,675,554 | * | 10/1997 | Cole et al. ........................ 367/138 |
| 5,911,692 | * | 6/1999 | Hussain et al. ................... 600/447 |
| 6,014,897 | * | 1/2000 | Mo ..................................... 73/628 |
| 6,102,860 | * | 8/2000 | Mooney ............................ 600/443 |
| 6,115,326 | * | 9/2000 | Puma et al. ....................... 367/118 |

FOREIGN PATENT DOCUMENTS

WO94/21388    9/1994  (WO).

* cited by examiner

Primary Examiner—Marvin M. Lateef
Assistant Examiner—Ali M. Imam

(57) ABSTRACT

An ultrasound transducer system is provided which produces a wide area scan of a body being imaged. The ultrasound transducer includes an array of N×M transducer elements, with the transducer elements preferably arranged in columns and rows. The transducer array comprises M columns of N elements each, with M and N being integers. The ultrasound transducer system further includes a transmitter for generating transmission signals and a receiver for receiving and processing ultrasound backscatter signals. A first switching arrangement sequentially connects the transmitter to subarrays of N×X transducers each so as to sequentially energize the subarrays to generate ultrasound interrogating beams across the face of the array. A second switching arrangement is provided which sequentially couples the receiver to each energized subarray to enable the reception and processing of acoustic signals from each subarray, in sequence. Because each individual subarray is steered only in the elevational direction, only the N transducers need to be spaced $\leq 0.5\lambda$. Transducers spaced along the long axis of the array may be spaced up to $2\lambda$ apart.

7 Claims, 2 Drawing Sheets

SYSTEM AND METHOD EMPLOYING TWO DIMENSIONAL ULTRASOUND ARRAY FOR WIDE FIELD OF VIEW IMAGING

FIELD OF THE INVENTION

This invention relates to ultrasound imaging systems and, more particularly, to a method and apparatus for operating a two dimensional array of ultrasound transducers to enable imaging of a wide field of view.

BACKGROUND OF THE INVENTION

Currently, ultrasound transducers of the type used in medical imaging mainly employ one-dimensional element arrays. Such an array comprises a linear grouping of transducer elements, wherein transmitted pulses are steered and dynamically focused only along the long dimension of the array. Transducers employing two dimensional element arrays are also known, however, the few two dimensional (2D) arrays that have been built to date are sector scanners. More particularly, the point of origin of a beam from such a 2D array is generally fixed in the center of the array and is scanned by appropriate phasing of the individual transducer elements of the array.

For certain types of imaging, e.g., abdominal imaging, linear arrays are typically used which translate the beam across the transducer face and thus form an image with a wide field of view at the skin surface.

Examples of two dimensional ultrasound arrays may be found in published PCT Application WO 94/21388 to Thomas et al. and U.S. Pat. No. 5,427,106 to Breimesser et al. A further example of a two dimensional ultrasound array is disclosed in U.S. Pat. No. 5,460,180 to Klepper et al. The Klepper et al. array comprises two different size transducer elements. Large transducer elements are positioned in the central portions of the transducer array, while more finely segmented transducer elements positioned at the ends of the array.

The Klepper et al. system is used to correct phase distortions of backscattered wavefronts which occur when the ultrasound signal propagates through an inhomogeneous medium, such as the human body. Such phase distortions occur as a result of variations in index of refraction through the tissues in the body. The effect of distortion in the elevation dimension is to produce a phase cancellation caused by a phase sensitive integration of the signal over the elevation dimension of the array elements. The approach used by Klepper et al. to correct for this phase distortion is to utilize the more finely segmented transducer elements, in combination with stepped groups of larger transducer elements, so as to enable the signals from the more finely segmented transducer elements to be utilized for the correction of the signals from the larger transducer elements. Such a correction scheme is implemented by sequentially multiplexing groups of the larger transducer elements across the face of the transducer along with a common connection of the finer transducer elements at the end of the transducer.

In substantially all of the linear, two dimensional transducer arrays of the prior art, the pitch between the transducer elements is generally maintained equal to or less than one half of the wavelength of the principal frequency emitted by the transducer. If the pitch distance between the elements is increased to greater than this value, acoustic beam side lobe signals are developed in the scan direction which tend to interfere with returning signals from the principal lobe direction. As a result, ultrasound units require large numbers of transducer elements that are closely spaced to avoid such side lobe projection in the scan dimension. In some cases, only a subset of the elements are used (known as a "sparse array"). This reduces element count but raises side lobe levels and causes a reduction in image quality.

There is a need for a two-dimensional wide area ultrasound scanning transducer that utilize a lesser number of transducers than are present in prior art arrangements and avoids side lobe generated signal anomalies.

SUMMARY OF THE INVENTION

An ultrasound transducer system is provided which produces a wide area scan of a body being imaged. The ultrasound transducer includes an array of N×M transducer elements, with the transducer elements preferably arranged in columns and rows. The transducer array comprises M columns of N elements each, with M and N being integers. The ultrasound transducer system further includes a transmitter for generating transmission signals and a receiver for receiving and processing ultrasound backscatter signals. A first switching arrangement sequentially connects the transmitter to subarrays of N×X transducers each so as to sequentially energize the subarrays to generate ultrasound interrogating beams across the face of the array. A second switching arrangement is provided which sequentially couples the receiver to each energized subarray to enable the reception and processing of acoustic signals from each subarray, in sequence. Because each individual subarray is steered only in the elevational direction, only the N transducers need to be spaced $\leq 0.75\lambda$. Transducers spaced along the long axis of the array may be spaced up to $2\lambda$ apart.

DETAILED DESCRIPTION OF A PREFERRED EMBODIMENT

Figure 1:
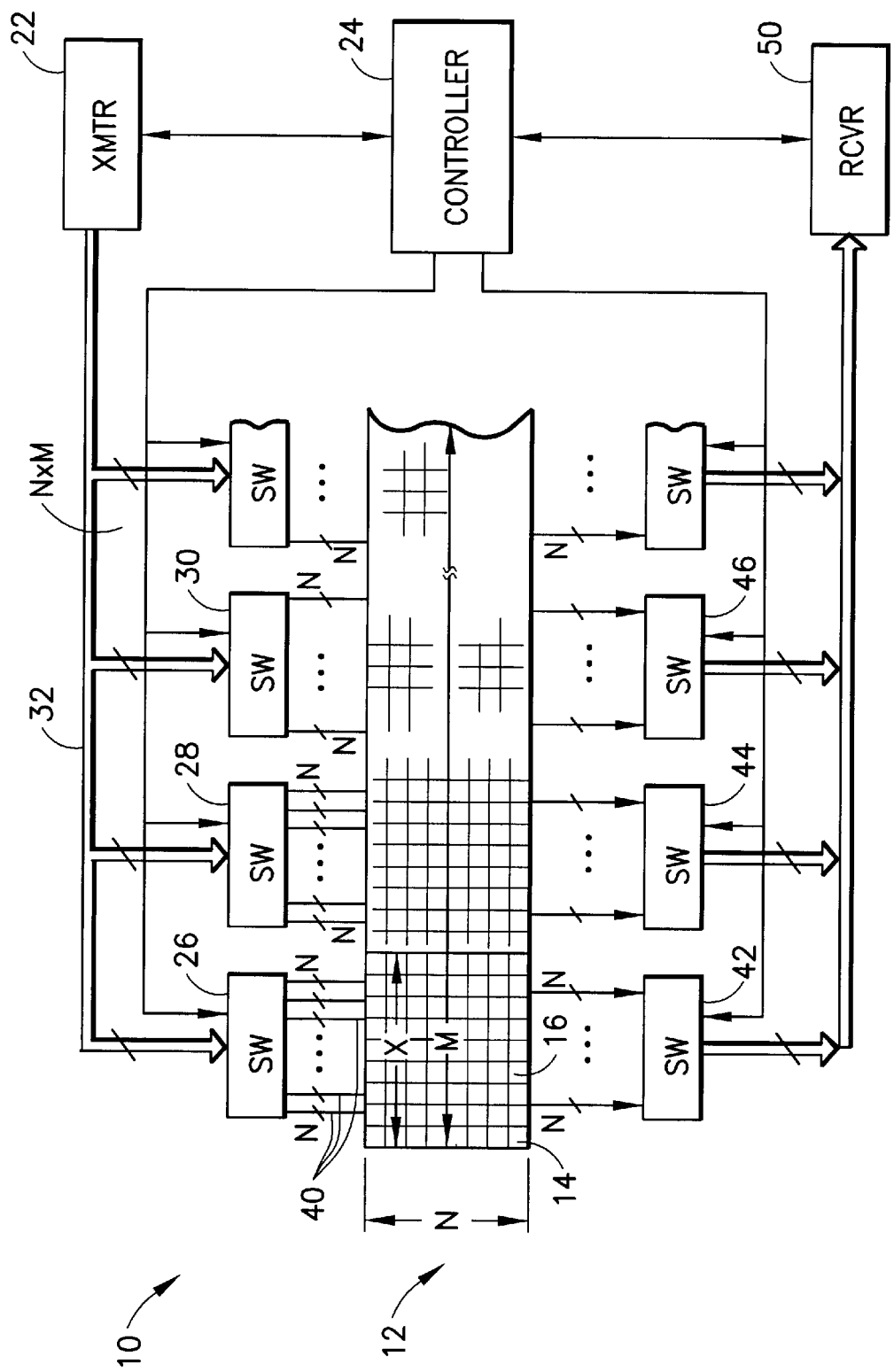
FIG. 1 is a schematic block diagram illustrating an embodiment of the invention.

Referring to FIG. 1, a schematic view of ultrasound system 10 is illustrated which utilizes a phased array 12 of individual ultrasound transducer elements. Array 12 is shown face-on and comprises, for example, a rectangular matrix of transducer elements 14 that are arranged in columns and rows. Ultrasound array 12 is comprised of M columns of N transducer elements each. During operation, input switches energize a subarray (e.g., subarray 16) of N×X transducer elements 14 to form an ultrasound beam. During a next cycle, the connected switches increment (i.e., move) the subarray by one column of transducer elements and apply appropriate energizations to the next N×X subarray of transducer elements 14. In such manner, the subarray is stepped along the face of array 12. One skilled in the art will understand that there are other techniques for translating the beam laterally along the array (e.g., half-stepping).

By properly phasing signals fed to individual transducers elements 14 of each energized subarray, an ultrasound beam that emanates from each subarray (i.e., out of the page towards the viewer) can be swept in elevation. More particularly, if signal pulses applied to each column of N transducers are all in phase, then the transmitted beam is orthogonal to the page. By altering the relative phasing of the signal pulses, the respective ultrasound signals emanating from the individual transducers 14 can be made to be additive in an direction that varies from the orthogonal by plus or minus Θ degrees, depending upon the signal pulse phasing differences applied to transducer elements 14. In addition, limited phasing of the summed signals from the elements of each column can provide beam focussing and limited steering in the lateral direction.

Ultrasound system 10, comprises a transmitter 22 which, under control of a controller 24 provides energizing pulses to each of a plurality of multiplexing switches 26, 28, 30, etc. Bus 32 emanating from transmitter 22 comprises N×X lines, each line adapted to carry a phased energizing pulse to be applied to one of transducer elements 14. Bus 32 is connected to each of switches 26, 28 and 30 so that each switch is "in parallel". Controller 24 connects to each of switches 26, 28, 30, etc. and controls each thereof so as to enable stepped application of energizing pulses to transducer elements 14 in the succeeding subarrays that are energized. Each of switches 26, 28, 30, . . . outputs X buses 40, each bus 40 comprising N lines carrying energizing pulses to the N ultrasound transducer elements 14 which comprise a column.

Accordingly, for instance, when switch 26 is turned on by controller 24 (with transmitter 22 being operated to generate N×X energizing pulses on bus 32), each of the N×X transducer elements 14 in subarray 16 (for example) is energized by the pulse outputs on a bus 40. Accordingly, subarray 16 outputs an ultrasound interrogating beam whose direction is dependent upon the respective phasing of the energizing pulse signals applied to individual transducers elements 14.

Switches 26 and 28 are next energized to increment the subarray by one column of transducer elements 14 so that the N×X array moves by one column to the right. Appropriate energizizng signals are then applied to bus 32 so as to energize the transducer elements of the connected array. Accordingly, the transmitted ultrasound beam is first generated from subarray 16; then from a next subarray, incremented by one column of transducer elements; then from a nest subarray incremented by one column of transducer elements, etc., until all transducer elements 14 have been operated.

Immediately subsequent to a transmission action by a respective subarray, controller 24 operates a respectively associated switches 42, 44, 46, etc. so as to connect transducer elements 14 in the energized subarray to an output bus arrangement 48 which feeds receiver circuitry 50.

Figure 2:
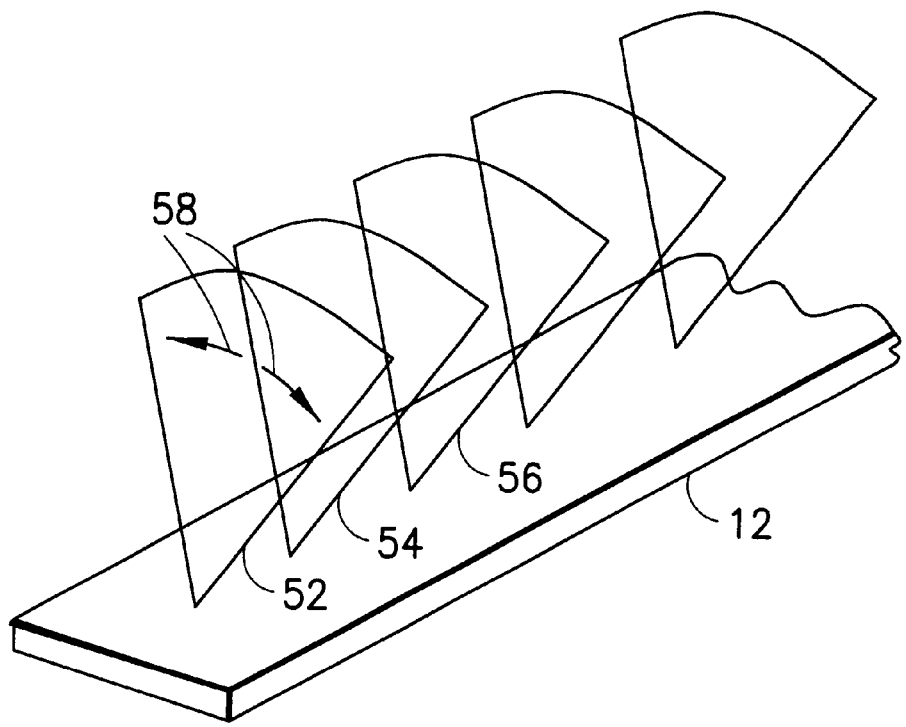
FIG. 2 schematically illustrates the swept beams that emanate from the ultrasound transducer of FIG. 1.

FIG. 2 illustrates, schematically, beams 52, 54, 56, etc., as they are respectively generated by substantially separated subarrays of transducer elements 14. During each application of energizing pulses to a subarray, phase alterations applied to the energizing pulses enables elevational sweeping of the output beams (as shown by arrows 58). As can thus be seen, the overall arrangement of the subarrays enables an elongated wedge of tissue to be imaged by ultrasound transducer 12.

Figure 3:
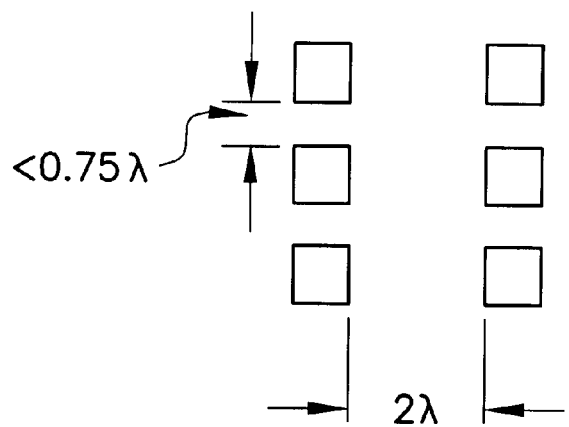
FIG. 3 is an expanded view of a plurality of transducer elements present in the ultrasound transducer of FIG. 1.

The arrangement of transducer elements 14 in the individual subarrays enables their longitudinal spacing to be up to $2\lambda$ apart if lateral steering of the beams is unneeded. The elevational spacing between adjacent transducer elements 14 should be $\leq 0.75\lambda$ (see FIG. 3). If there is to be lateral steering of the ultrasound beams along the long dimension of ultrasound transducer 12, the spacing along the lateral dimension between ultrasound transducers 14 should be reduced.

The point of origin of the beams which emanate from ultrasound transducer 12 can be offset from the center line the array to provide a wider elevation field of view at the surface. Further, a group of lateral columns of elements can be activated simultaneously (where less than N elements are active in selected columns), so as to activate a non-rectangular aperture, such as an ellipse to reduce the number of active elements.

It should be understood that the foregoing description is only illustrative of the invention. Various alternatives and modifications can be devised by those skilled in the art without departing from the invention. For example, while, for explanatory purposes separate switches have been shown for the transmit and receive actions, a preferred embodiment would employ common switches for both the transmit and receive functions. Accordingly, the present invention is intended to embrace all such alternatives, modifications and variances which fall within the scope of the appended claims.

What is claimed is:

1. An ultrasound transducer system for producing a wide area scan of a body, said system comprising:
   a transducer body comprising an array of N×M transducer elements, there being M columns of N transducer elements, wherein M and N are integers;
   transmitter means for generating transmission signals;
   receiver means for receiving and processing ultrasound backscatter signals;
   switch means for connecting said transmitter means to a plurality of subarrays of N×X transducer elements along said array, where X is an integer <M, so as to energize each of the transducer elements in each subarray to cause ultrasound beams to be generated therefrom; and
   control means for operating said switch means to sequentially connect said transmitter means and receiver means to each said subarray so as to enable reception by said receiver means of acoustic signals from an elongated sector volume.

2. The ultrasound transducer system as recited in claim 1, wherein said control means operates said switch means to sequentially couple said receiver means to each subarray N×X of transducer elements to enable reception and processing of acoustic signals from each energized subarray, subsequent to energization thereof by said transmitter means.

3. The ultrasound transducer system as recited in claim 1, wherein said transducers in a subarray are arranged in plural elevational columns and longitudinal rows.

4. The ultrasound transducer system as recited in claim 3, wherein N ultrasound transducer elements of an elevational column are separated by a distance of $\leq 0.75\ \lambda$, wherein $\lambda$ is the wavelength of a principal frequency signal that emanates from said ultrasound transducer elements, and wherein N ultrasound transducer elements of an elevational column are separated from N ultrasound transducer elements of an adjacent elevational column by a distance of about $\leq 2\lambda$.

5. The ultrasound transducer system as recited in claim 3, wherein said control means causes said transmitter means to alter phasing of energizing signals applied to ultrasound transducer elements positioned in columns so as to enable a steering of an ultrasound beam emanating therefrom.

6. The ultrasound transducer system as recited in claim 3, wherein said control means causes said transmitter means to selectively apply energizing signals to ultrasound elements of a subarray to alter a point of origin of an ultrasound beam that emanates from said subarray.

7. The ultrasound transducer system as recited in claim 3, wherein said control means causes said transmitter means to selectively apply energizing signals to a group of lateral columns of ultrasound elements simultaneously so as to activate a non-rectangular aperture.

* * * * *